(12) United States Patent
Wilk et al.

(10) Patent No.: US 8,737,439 B2
(45) Date of Patent: May 27, 2014

(54) OPTICAL ASSEMBLY AND METHOD FOR GENERATING LIGHT PULSES OF VARIABLE DELAY

(71) Applicants: Rafal Wilk, Martinsried (DE); Ronald Holzwarth, Munich (DE); Michael Mei, Steinebach (DE)

(72) Inventors: Rafal Wilk, Martinsried (DE); Ronald Holzwarth, Munich (DE); Michael Mei, Steinebach (DE)

(73) Assignee: Menlo Systems GmbH, Martinsried (DE)

( * ) Notice: Subject to any disclaimer, the term of this patent is extended or adjusted under 35 U.S.C. 154(b) by 0 days.

(21) Appl. No.: 13/748,026

(22) Filed: Jan. 23, 2013

(65) Prior Publication Data

US 2013/0188661 A1 Jul. 25, 2013

(30) Foreign Application Priority Data

Jan. 24, 2012 (DE) .......................... 10 2012 001 357

(51) Int. Cl.
*H01S 3/10* (2006.01)

(52) U.S. Cl.
USPC .................... 372/25; 372/23; 372/34; 372/18

(58) Field of Classification Search
USPC ......................................... 372/25, 23, 34, 18
See application file for complete search history.

(56) References Cited

U.S. PATENT DOCUMENTS 5,778,016 A * 7/1998 Sucha et al. ................. 372/38.1
2009/0073432 A1 3/2009 Jalali et al.
2010/0225897 A1 9/2010 Fermann et al.
2010/0282970 A1 11/2010 Haran et al.
2011/0141540 A1 * 6/2011 Hochrein et al. ............. 359/238
2011/0170171 A1 * 7/2011 McCallion et al. ........... 359/325

FOREIGN PATENT DOCUMENTS

DE 10 2008 026 484 A1 12/2009

OTHER PUBLICATIONS

German Patent Office Search Report issued in German Application No. 102012001357.4 dated Oct. 23, 2012 (5 pages).
R. Wilk: "All fiber THz spectrometer for plastics industry" In: Bulletin of the Polish Academy of Sciences, Technical Sciences, vol. 59, No. 3, 2011, S. 283-285.

* cited by examiner

*Primary Examiner* — Kinam Park
(74) *Attorney, Agent, or Firm* — Flynn, Thiel, Boutell & Tanis, P.C.

(57) ABSTRACT

The invention relates to an optical assembly (1) comprising a pulsed light source (2) for generating primary light pulses (4), a pulse splitter (5) for splitting said primary light pulses (4) into first and second secondary light pulses (7), and a delay element (8) for delaying said second secondary light pulses (7) relative to said first secondary light pulses (6), where the pulse repetition rate of said pulsed light source (2) is variable in order to change a temporal delay between different secondary light pulses (6,7) The invention is characterized in that said optical assembly (1) comprises a thermal insulation (12), a temperature stabilizer (16) or a temperature compensator (13) for said delay element (8) and/or a control circuit (27) for determining and controlling a drift of said pulse repetition rate.

9 Claims, 13 Drawing Sheets

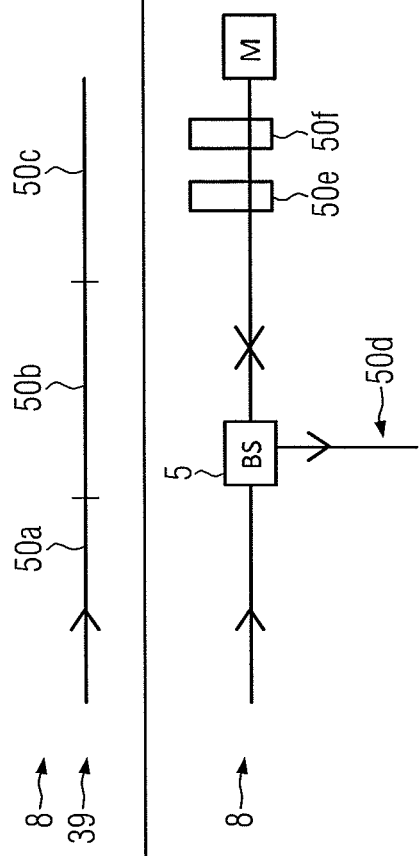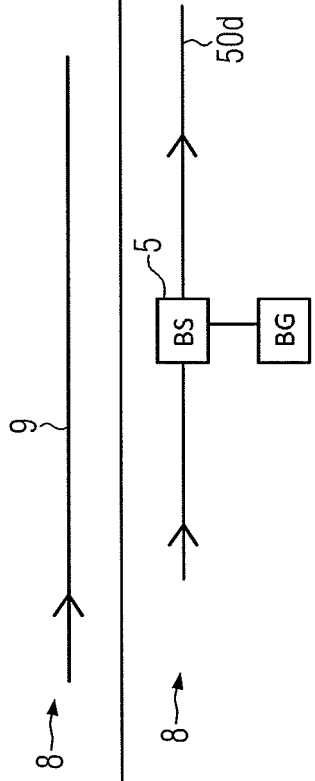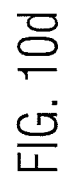

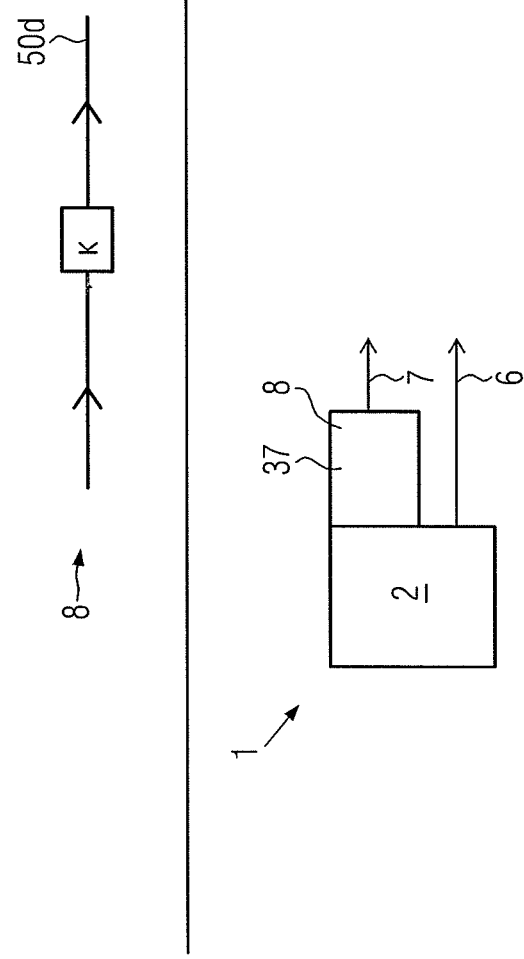

OPTICAL ASSEMBLY AND METHOD FOR GENERATING LIGHT PULSES OF VARIABLE DELAY

Figure 1:
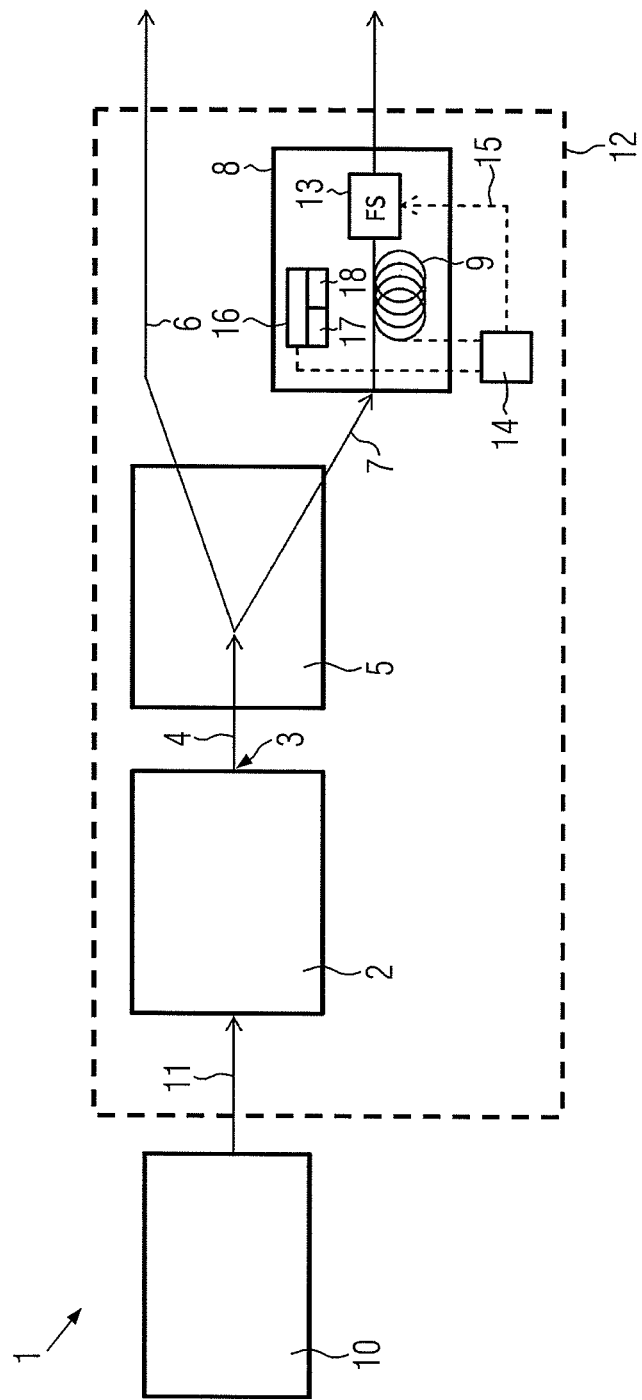

The invention relates to an optical assembly according to the preamble of claim 1 and to a corresponding method.

A generic optical assembly and a corresponding method are known under the title "Optical sampling by cavity tuning (OSCAT)", for example, from DE 10 2008 026 484 A1, from the article "Optical sampling by laser cavity tuning," T. Hochrein, R. Wilk, M. Mei, R. Holzwarth, N. Krumbholz, M. Koch, OPTICS Express 1613, vol. 18, no. 2, January 2010, or from the article "OSCAT: Novel Technique for Time-Resolved Experiments Without Moveable Optical Delay Lines", R. Wilk, T. Hochrein, M. Koch, M. Mei, R. Holzwarth, J Infrared Milli Terahz Waves (2011) 32:596-602.

The principle behind the OSCAT method is based on the fact that a pulsed light source emits a sequence of light pulses. These light pulses are split to a pulse or beam splitter in sequences of first and second secondary light pulses. There is a delay line or generally a delay element, respectively, in the path passed by the second secondary light pulses, which provides for a temporal delay of the second secondary laser pulses relative to the first secondary laser pulses. The OSCAT method now enables variably adjusting a temporal delay for a certain second secondary light pulse relative to a first secondary light pulse, even if the temporal delay of the second secondary light pulses caused by the delay element remains constant or when the optical path length of the delay element remains constant, respectively. This is achieved by changing the repetition rate or (synonymously) the pulse repetition rate of the pulsed light source. For this purpose, for example, a resonator length of the pulsed light source can be varied.

The adjustable delay of the two light pulses relative to each other allows a number of unique applications, for example in terms of spectroscopic examinations or so-called pump-probe experiments, THz time-domain spectroscopy or Fourier transform spectroscopy. Compared to alternative systems for creating a variable delay of two light pulses relative to each other, the OSCAT method provides enormous advantages in terms of robustness and lower adjustment effort and lower costs. For example, in the past, an optical delay line was changed mechanically, usually by moving one or more mirrors in order to effect the change of the delay. This, however, required a high level of adjustment effort and a disproportionately high amount of time and effort for the mechanical precision of the movement. In another method, the so-called "Asynchronous Optical Sampling (ASOPS)", two pulsed light sources are used and electronically synchronized with each other. This, however, meant very high costs and additional effort for the electronic synchronization due to the two pulsed light sources. A similarly complex method using two synchronic lasers is described in U.S. Pat. No. 5,778,016 A.

The object of the present invention is to improve the conventional optical assembly or the conventional method, respectively, in terms of their possible applications.

This object is solved by an optical assembly having the features of one of the claim 1 or 6, and by a method having the features of claim 8, respectively. Advantageous developments of the invention are disclosed in the dependent claims.

The optical assembly according to the invention comprises a pulsed light source for generating primary light pulses. This pulsed light source is preferably, but not necessarily, a coherent pulsed light source, i.e. a pulsed laser. It could in particular be an amplitude-modulated CW-semiconductor laser, commonly however, a mode-locked laser like short pulse or ultrashort pulse lasers, for example, femtosecond lasers. As a pulsed light source, a continuous light source (such as a cw-laser) can alternatively be used with a variable (amplitude) modulation frequency. This pulsed light source generates a train of primary light pulses with a variable pulse repetition rate. In this, the pulse repetition rate or repetition rate is the frequency at which the pulsed light source emits the primary light pulses. Usually the pulse repetition rate is the inverse of the cycle time of a light pulse in a resonator of the pulsed light source. Synonymous to the term "pulsed light source", the expression "oscillator" may be used.

A pulse splitter is provided to split the primary light pulses into first and second secondary light pulses. The term pulse splitter also comprises beam splitters which direct a first portion of each primary light pulse into a first light path and the remaining portion of the primary light pulse into a second light path. The term pulse splitter, however, also comprises optical elements where the two light paths coincide so that the two secondary light pulses are emitted by the pulse splitter into a common path, but staggered behind each other. Only the second secondary light pulses are then subjected to a temporal delay being caused by a delay element. The optical path length of the delay element is that path length by which the length of the light path of the second secondary laser pulses differs from that of the first secondary laser pulses. This path length is usually fixed. The first and second secondary light pulses can then be directed to a target area, possibly be focused in this target area. In this, the target areas, to which the two secondary laser pulses are directed, can coincide or diverge. In a fiber-based embodiment of the optical assembly, a fiber coupler can be used as a pulse splitter. The pulse splitter, however, can also already be integrated in the pulsed light source, so that it comprises two output ports respectively emitting the first and the second secondary light pulses.

The optical assembly according to the invention now provides a thermal insulation for thermally insulating the delay element, a temperature stabilizer for thermally stabilizing the delay element, a temperature compensator for compensating a temperature-dependent change of an optical path length of the delay element and/or a control circuit for detecting and controlling a drift of a mean pulse repetition rate of the pulsed light source. These four measures are suitable individually as well as in any combination to significantly increase the precision of the temporal delay of two light pulses relative to each other, achieved with the optical assembly. This precision is in turn crucial for the accuracy and informative value of the applications or experiments performed with the delayed light pulses.

The thermal insulation of the delay element can be effected for instance by enclosing the delay element in temperature-insulating material such as polystyrene or styrene. The thermal insulation effects a decoupling of the temperature of the delay element from the ambient or room temperature. It is thereby prevented, that varying ambient temperature influences the delay element and in particular the optical path length of the delay element and thereby the delay of the light pulse caused by the delay element. For this, the delay element can be designed as a glass fiber.

A temperature stabilizer also causes a decoupling of the temperature of the delay element from the ambient or room temperature, in that it provides a way to keep the temperature of the delay element stable even with a change of ambient temperature. For example, a target temperature and a tolerance range around the target temperature could be provided for the temperature stabilizer in order to initiate a return of the temperature of the delay element to the target temperature when the actual temperature is out of the range of tolerance.

A temperature compensator in turn can accept a change in the temperature of the delay element. It offers the advantage, however, of being able to compensate a change of the optical path length of the delay element caused by the increase in temperature. For example, a temperature rise could lead to expansion of the delay element and thereby to an extension of the optical path length. The temperature compensator would be configured to compensate this extension of the optical path length by means of an element that would inversely experience reduction of a path length (and vice versa).

The three above-mentioned variants are all related to the delay element. Alternatively or additionally, it would be conceivable to control the pulse repetition rate of the pulsed light source using a control circuit—preferably by detecting the drift of a mean pulse repetition rate of the pulsed light source in a control circuit and to control the pulse repetition rate of the pulsed light source by means of the same control circuit such, that any drift is again compensated or reversed, respectively, to the highest degree possible. This would account for the fact that a change in the ambient temperature can influence not only the delay line, but also the pulsed light source itself.

When temperature insulation exists, it could in addition to the delay element also enclose the pulse splitter, preferably also the pulsed light source. In addition to the delay element, further components of the optical assembly would thereby be thermally insulated against the ambient temperature, so that a change in the ambient temperature can no longer influence the optical assembly and in particular the precision of the delay of the light pulses.

If a temperature stabilizer is provided, then it preferably comprises a temperature sensor and at least one heating element and/or at least one cooling element. The temperature sensor allows automation of the temperature stabilization in that it detects, for example, the temperature of the delay element. The measured value of the temperature sensor can then be suitably evaluated in order to control a heating element and/or a cooling element such, that the temperature of the delay element remains within a target range.

The optical assembly according to the invention becomes particularly robust when it largely or even completely dispenses with free-space beam paths and instead is configured fiber-optically. The delay element could in particular be a certain path length of a light wave conductor or an optical fiber. In this case, it would be conceivable to provide a controllable fiber stretcher as a temperature compensator. It can by means of a suitable actuator, for example, a piezo-electric actuator, engage the fibers of the delay element. If the temperature of that delay element changes and the fiber thereby expands or shortens, then the fiber stretcher could cause shortening or expansion of the fiber with the opposite sign, so that the optical path length of the delay element remains constant regardless of the temperature.

If a control circuit for detecting and controlling a drift of a mean pulse repetition rate of the pulsed light source is provided, then preferably a frequency detector, a frequency counter or a phase detector is used to determine the pulse repetition rate of the pulsed light source. In the optical assembly according to the invention, the pulse repetition rate of the pulsed light source, however, is specifically altered to change the delay of the light pulses.

One can stabilize the repetition rate to a fixed value by means of the phase detector (so-called PLL, phase locked loop) For scanning the repetition rate, one can then apply a modulation between the output of the phase detector and the input of the "lockbox" (PI-circuit).

In order to disregarded the selectively induced change of the pulse repetition rate with regard to temperature compensation and instead to measure only a mean drift of the pulse repetition rate, the signal from the frequency detector, the frequency counter, or from the phase detector can optionally be filtered via a low pass filter.

This filter blocks the selectively induced change of the pulse repetition rate, however, lets pass a drift or low-frequency change of the pulse repetition rate. The filtered signal can then be fed to a controller, which by mean of a suitable actuator can influence, for example, an electro-optical (EOM) modulator, can have influence on the resonator length of the pulsed light source, or by means of an amplitude modulator (AM) on the continuous-wave source, and hence on its pulse repetition rate.

When a frequency counter is used, one can select its gate time such that it replaces the low-pass. Then one could read out the counter and adjust the repetition rate accordingly.

Use of a low-pass makes most sense when a frequency detector is used, i.e. a device that supplies a voltage in dependency on the present frequency. In this manner, no phase lock (i.e. coupling of the phases) is possible, but only a frequency lock, which is basically slightly more inaccurate, because not the phase (i.e. directly the sine wave motion) is tracked. For most applications, however, already this accuracy should be quite sufficient In an even simpler variant, the optical assembly monitors the temporal position of the pulse in the experiment. If the pulse drifts, the system adjusts the pulse repetition rate.

It is also conceivable that the control circuit comprise a function generator for setting a constant or variable external reference frequency. In this case, the external reference frequency can be compared with the signal passing through the low-pass filter and be appropriately evaluated.

In addition to the variants described above for temperature insulation, stabilization or compensation or also independent thereof, it can be provided that the optical assembly comprises one or more of the following elements in the optical path of the first and/or second secondary light pulses: an amplifier, an attenuator, a non-linear medium, a second-harmonic generator (SHG), a pulse compressor, a pulse picker, an amplitude modulator and/or a dispersion compensator.

Each of these elements, and in particular combinations of these elements significantly increases the functionality of the optical assembly. An amplifier can be realized in the form of an optically pumped and suitable fiber optical line doped with foreign atoms. In this, variants are conceivable in which an amplifier is provided only for the first or only for the second secondary light pulses, respectively, or where a separate amplifier is provided for each of the first and second secondary laser pulses, in order to increase the peak intensity or the pulse energy of these pulses. A variant is also further conceivable in which the first and the second secondary laser pulses are united and passed into a common amplifier which is therefore provided for both the first as well as for the second secondary laser pulses. The latter variant has the advantage of being able to amplify both the first as well as the second secondary laser pulses, without having the need of providing a second amplifier. A variant is also conceivable in which an amplifier is used as a delay element if the amplifier itself can cause an extension of an optical path length, and thus a delay of light pulses. All these options are analogously also valid for an attenuator instead of an amplifier.

If a non-linear medium or a generator for the second or a higher harmonics is disposed in the path of the first and/or second secondary laser pulses, then this further increases the options of application of the optical assembly because, with these elements, the spectra of the leading or the delayed laser pulses, respectively, can be varied.

Other new applications arise when a pulse compressor, a pulse picker and/or an amplitude modulator are provided. A pulse compressor shortens the temporal duration of the first and/or the second light pulses.

A dispersion compensation of the optical delay line itself is therewith no longer necessary, since the compression is performed "at the end". This is also possible (e.g., in a free-space grating compressor) with much higher pulse energies than would be possible in fiber optic components.

It thereby allows for both higher peak intensities of the light pulses as well as a higher temporal precision, for example, for pump-probe experiments. A pulse picker allows selectively picking one or more light pulses in order to be able to examine e.g. the overall radiation of a sample. An amplitude modulator, however, allows for varying the amplitude in a train of light pulses. It is in this manner possible, to not only adjust the delay between the two laser pulses at the destination but also to delay the amplitude of the leading and/or trailing laser pulses. This allows obtaining both time—as well as intensity-dependent information of a sample into which the first and second secondary laser pulses are passed.

A dispersion compensator could be of particular interest, which leads to either the dispersion of the first secondary laser pulses exactly corresponding to that of the second secondary laser pulses as they each leave the optical assembly, or to the overall dispersion of the first and/or the second secondary laser pulses being as close to zero as possible.

A first option for a delay element with dispersion compensation is the coupling of two or more fiber types having inverse dispersion properties, so that the overall fiber line has effectively zero dispersion. For example, a so-called IDF (inverse dispersion fiber), a DCF (dispersion compensating fiber) or an SMF (single mode fiber), both in the form of a polarization-maintaining, as well as a non-polarization-maintaining fiber can be used. A second option lies in combining a polarization beam splitter, a circulator, non-polarization-maintaining IDF, DCF, and SFM fibers, λ/4-wave plates and a Faraday rotator. A third option is the use of a type of fiber that effectively has zero dispersion, for example, a dispersion-shifted fiber (DSF), a photonic crystal fiber, a hollow-core fiber, or a fiber with reduced non-linearities, again in the form of a polarization-maintaining or non-polarization maintaining fiber. A fourth option is the use of a fiber-Bragg grating and a single-mode fiber as well as a circulator and a beam splitter. Again, this version can be embodied as being polarization-maintaining or non-polarization-maintaining. A fifth option is a combination of a reflection grating or transmission grating with prisms for dispersion compensation of the first or a higher order. A further option is the use of fiber amplifier lines with non-linear dispersion adaptation (fiber modulation) or so-called parabolic pulse propagation.

The invention further relates to a method of generating light pulses with a variable delay time on the basis of the conventional OSCAT method. According to the method of the invention, the temperature of the delay element is maintained constant by means of a temperature stabilizer, a temperature-dependent change of an optical path length of the delay elements is compensated by means of a temperature compensator and/or a drift of the mean pulse repetition rate of the pulsed light source is determined and controlled as has been described in detail above. The technical advantage of these measures is particularly high precision of the temporal delay between different light pulses.

In this it would be conceivable, in particular, that the pulse repetition rate of the pulsed light source be determined by means of a frequency detector, a frequency counter, or a phase detector and a signal of the frequency counter or the phase detector, respectively, is also optionally filtered by means of a low-pass filter to determine the low-frequency drift of the pulse repetition rate.

Figure 2:
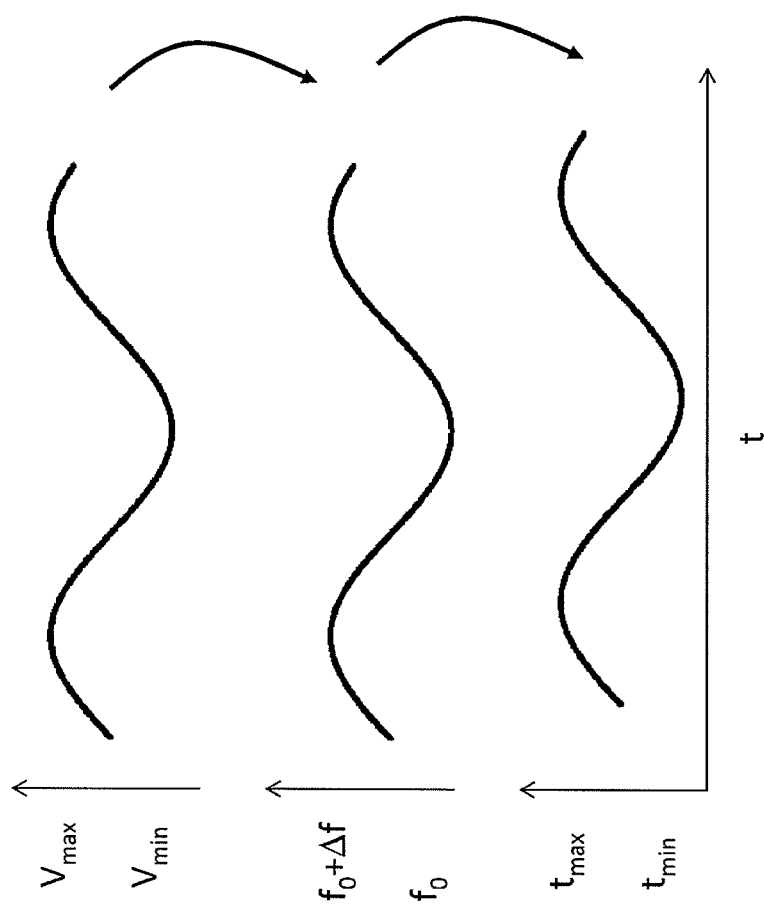
Figure 3:
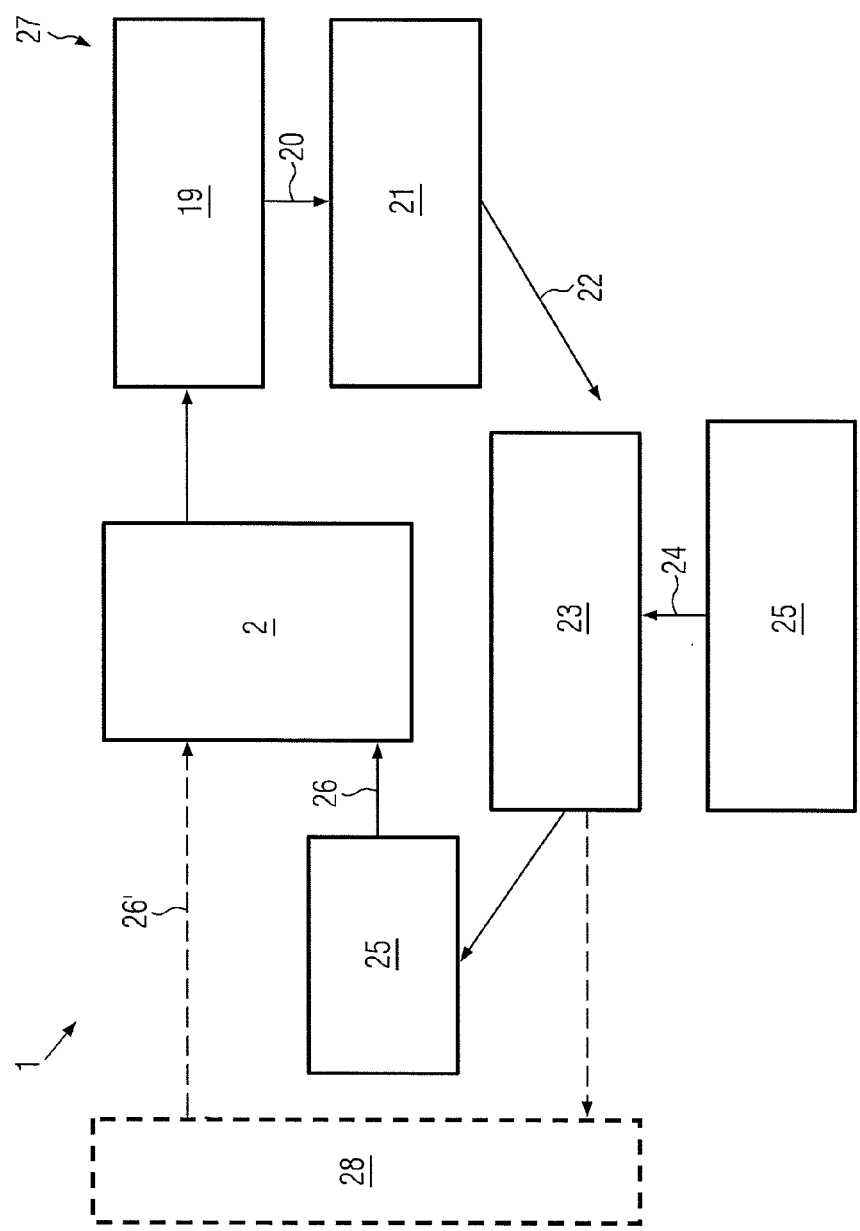
Figure 4:
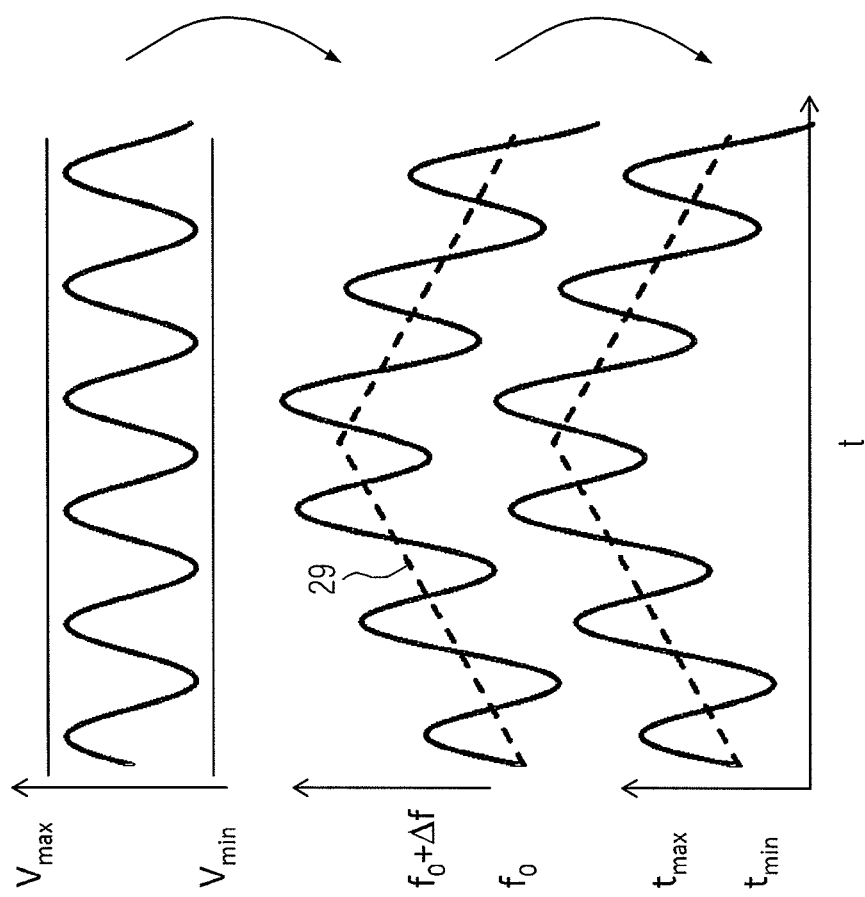
Figure 5:
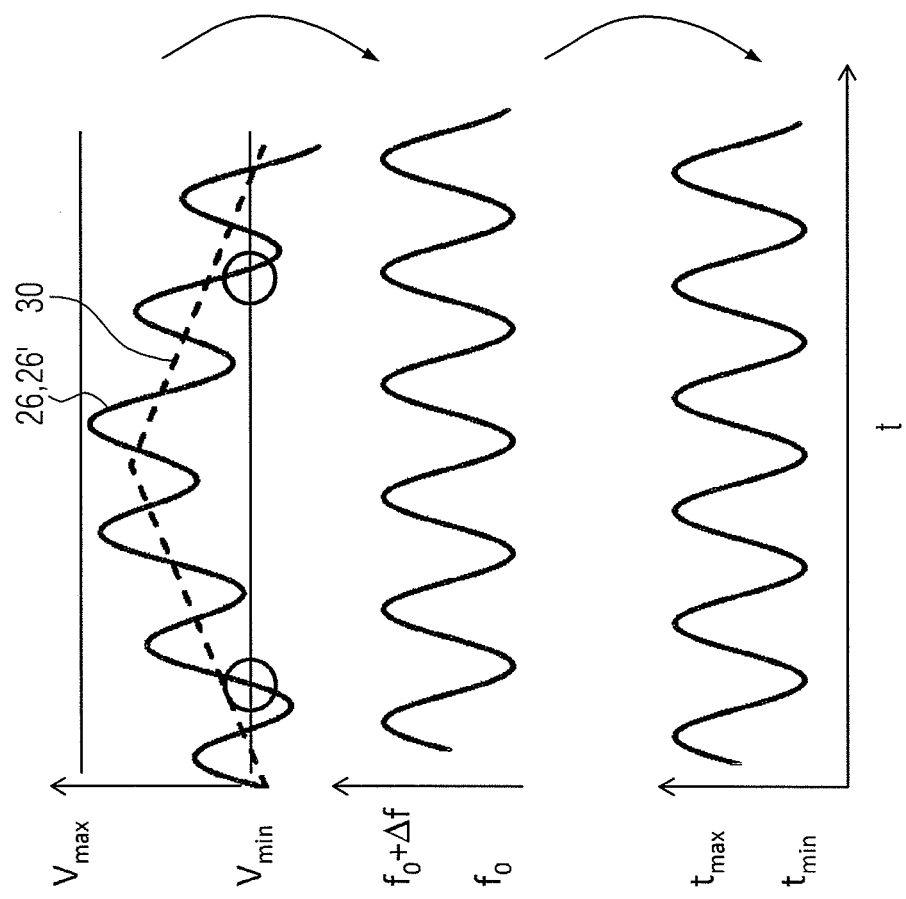
Figure 6:
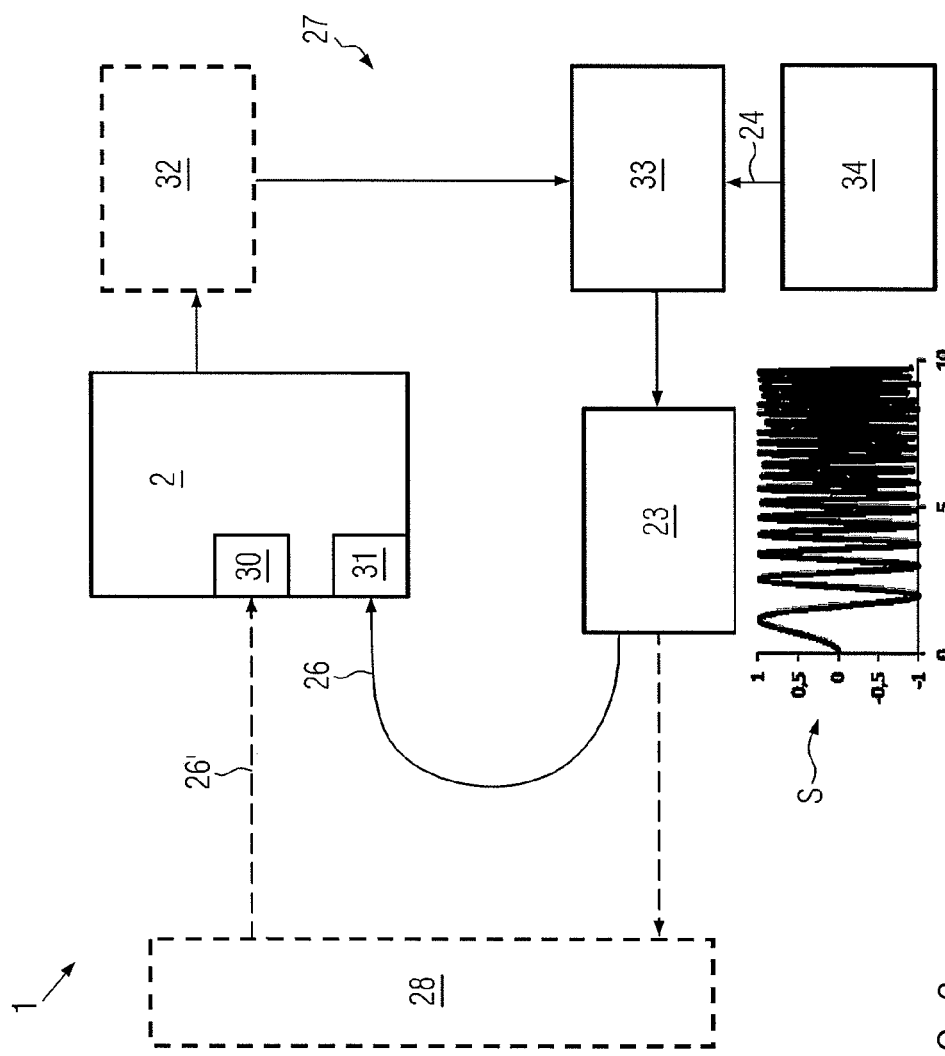
Figure 7:
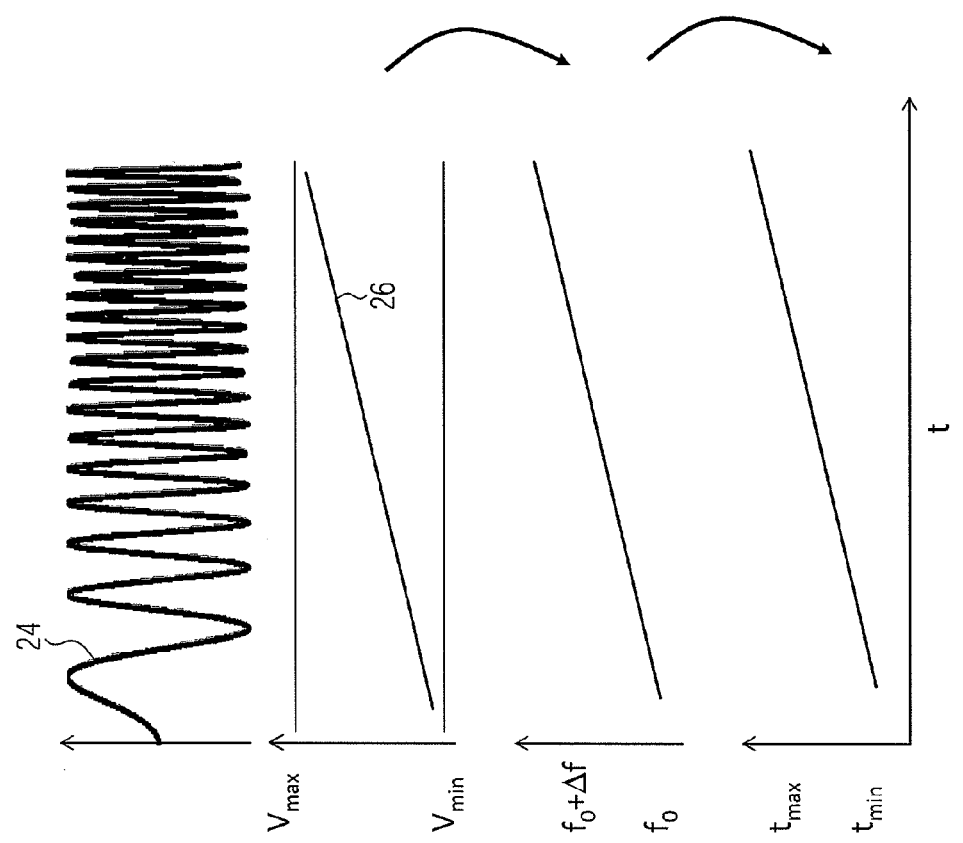
Figure 8:
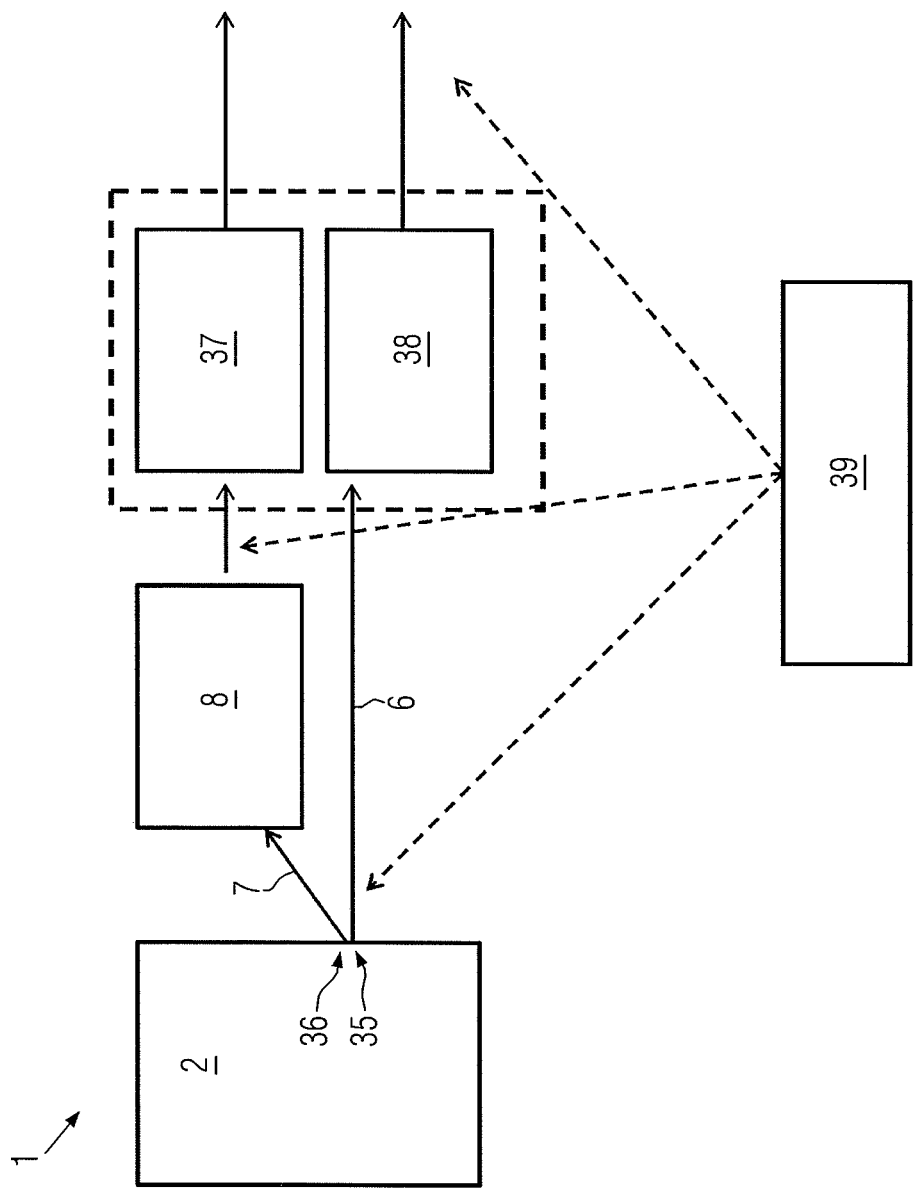
Figure 9:
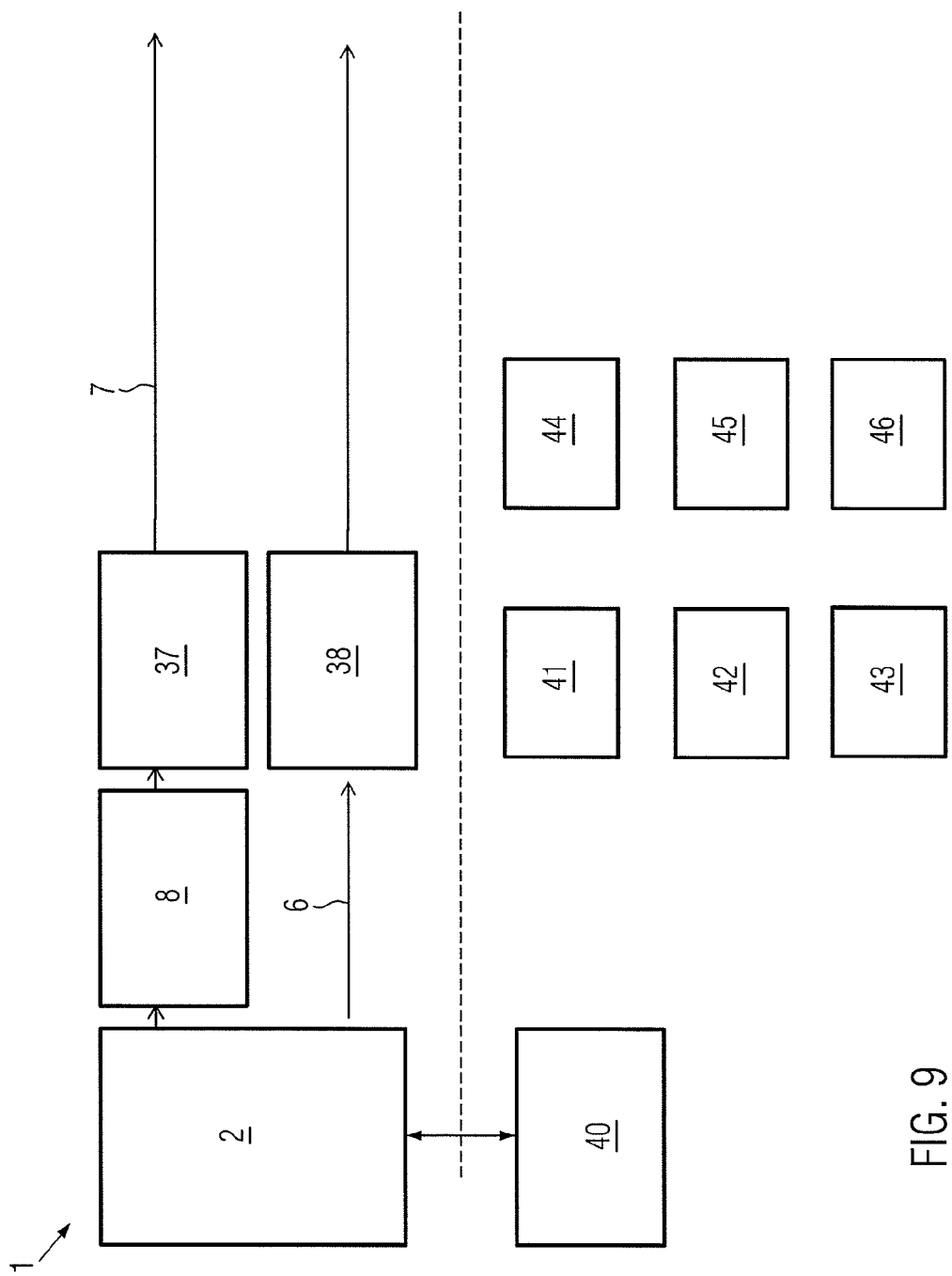
Figure 11:
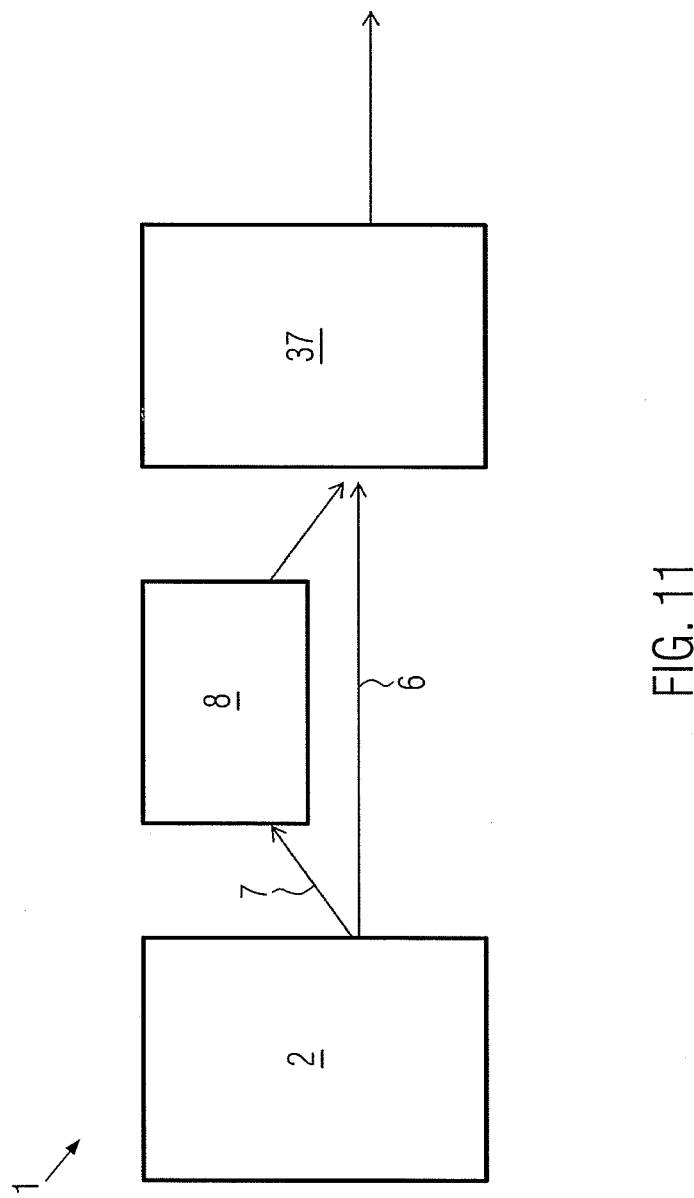
Figure 12:
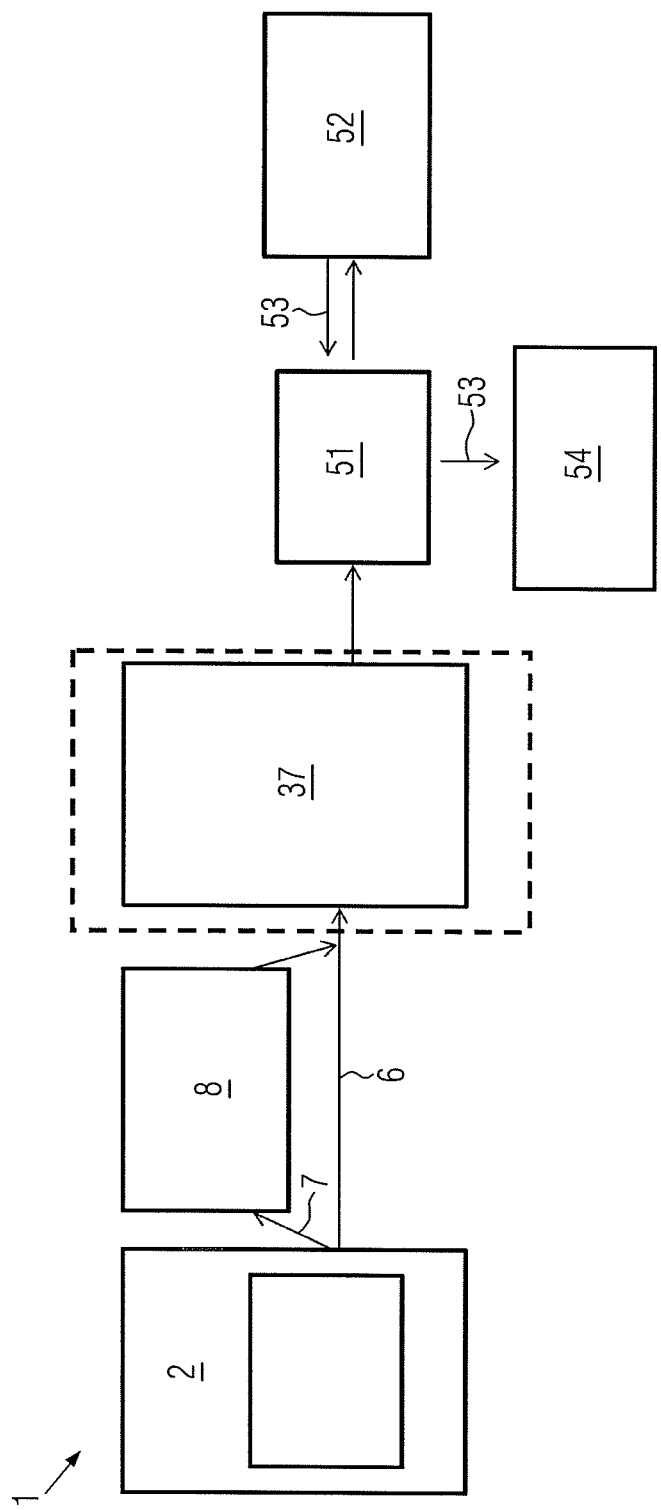

In the following, advantageous embodiments of the invention are further explained in detail by means of a drawing. Specifically:

FIG. 1: shows a schematic representation of a first embodiment of an optical assembly according to the invention, FIG. 2: shows a diagram for illustrating the temporal delay of the pulses, FIG. 3: shows a second embodiment of an optical assembly according to the invention, FIG. 4: shows a diagram for explaining the operation of the optical assembly shown in FIG. 3, FIG. 5: shows a further diagram for explaining the mode of operation of the optical assembly shown in FIG. 3, FIG. 6: shows a third embodiment of an optical assembly according to the invention, FIG. 7: shows a diagram for illustrating the mode of operation of the optical arrangement shown in FIG. 6, FIG. 8: shows a fourth embodiment of an optical assembly according to the invention, FIG. 9: shows a fifth embodiment of an optical assembly according to the invention, FIGS. 10a-10f show different variants of delay elements, FIG. 11: shows a schematic representation of a further embodiment of an optical assembly according to the invention and FIG. 12: shows a schematic representation of a further embodiment of an optical assembly according to the invention.

Identical components are in the figures designated throughout with the same reference numerals.

FIG. 1 shows a schematic representation of a first embodiment of an optical assembly 1 according to the invention. This optical assembly 1 is designed to generate light pulses with an adjustable or variable delay time between different pulses. For this purpose, the optical assembly 1 comprises an oscillator or a pulsed light source 2, respectively, for example, a short-pulse or an ultrashort-pulse laser. In the embodiment according to FIG. 1, the pulsed light source 2 comprises an output port 3 from which a train of primary laser pulses 4 exits the pulsed light source 2. In this, the repetition rate or the pulse repetition rate, respectively, of the primary light pulses 4 is variable, for example, in that a resonator length of the pulsed light source 2 is varied by control members such as piezo-electric actuators.

The optical assembly 1 further comprises a beam or pulse splitter 5. It has the function to split the primary light pulses into first and second secondary light pulses 6, 7, which leave the pulse splitter 5 on a first or on a second path, respectively, spatially separated therefrom. In this, in particular, each of the primary light pulses 4 are split in the pulse splitter 5 into a first portion which leaves the pulse splitter 5 as the first secondary light pulse 6 and a second portion which leaves the pulse splitter 5 as the second secondary light pulse 7. For example, a fiber-optic splitter or free-space beam splitter could be used as such a pulse splitter, for example, a 50:50 beam splitter, but also a beam splitter with a different splitting ratio.

The optical assembly 1 in the path of the second secondary laser pulses further comprises a delay element 8. The delay element 8 in the present embodiment comprises a delay fiber line 9. It serves to delay the second secondary light pulses 7 relative to the first secondary light pulses 6, in that the second secondary light pulses must in contrast to the first light pulses additionally pass through the optical path length of the delay element 8. This optical path length results from the location-dependent refractive index of the delay element 8, integrated across its geometrical length.

Already with the components described above, the optical assembly 1 is, by varying the repetition rate of the pulsed light source 2, capable of variably adjusting the temporal delay between the first and the second secondary light pulses 6, 7. For varying the repetition rate or the pulse repetition rate, respectively, of the pulsed light source, the optical assembly 1 comprises a signal generator 10. This signal generator 10 for example generates a sinusoidal or sawtooth-shaped signal which is fed to the pulsed light source 2. The input signal is in the pulsed light source 2 converted into a corresponding change of the pulse repetition rate.

In the embodiment of FIG. 1, the optical assembly 1 comprises a thermal insulation 12, for example, a jacket of thermally insulating material. The insulation 12 thermally insulates the components it envelopes from the environment. In the present embodiment, the pulsed light source 2, and the pulse splitter 5 and the delay element 8 are located within the thermal insulation 12. In a simpler configuration, however, it would be sufficient for many applications, if only the delay element 8 would be surrounded by thermal insulation 12 in order to thermally insulate the delay element 8. In this manner, the delay element 8 does not participate in the changes in the ambient temperature. It therefore maintains its optical path length, so that the delay of the light pulses generated by the optical assembly 1 is precisely adjustable.

In the embodiment shown in FIG. 1, the optical assembly also comprises a temperature compensator 13. In the present embodiment, this temperature compensator 13 is designed as a controllable fiber stretcher FS. It has the task of compensating any temperature-related change of an optical path length of the delay element 8, if, in spite of the thermal insulation 12, there should be a slight change in temperature of the delay element 8. If, for example, during a temperature increase, the optical path length of the delay fiber line 9 of the delay element 8 increases, then the temperature compensator 13 could compensate for this by suitable reduction of an optical fiber and vice versa. A temperature sensor 14 is provided to measure the temperature of the delay element 8, in particular of the delay fiber line 9. The measurement signal of the temperature sensor 14 can be used as an input variable 15 for controlling the temperature compensator 13. Moreover, it can be used for controlling a temperature stabilizer 16 being provided in or at the delay element 8. This temperature stabilizer 16 comprises at least one heating element 17 and/or one cooling element 18. These elements are used to maintain the temperature of the delay element 8 as much as possible within a target range around a target value. The thermal insulation 12, the temperature stabilizer 16, and the temperature compensator 13 can also be provided individually and independently from each other in an optical assembly 1 according to the invention.

FIG. 2 shows a schematic representation of the adjustment of a temporal delay of two secondary light pulses 6, 7. For this purpose, FIG. 2 shows three curves on a time axis. The top curve represents the course of the input signal 11, with which the pulsed light source 2 is loaded. This input signal 11, however, varies periodically between a minimum voltage $V_{min}$ and a maximum voltage $V_{max}$.

The center curve shows the change of the pulse repetition rate of the pulsed light source 2 over time. This pulse repetition rate varies analogously to the input signal 11 between a minimum value $f_0$ and a maximum value $f_0+\Delta f$.

The bottom curve, finally, shows the temporal distance between two specific secondary light pulses 6, 7. This can be the temporal distance of two secondary pulses 6, 7, which originated from a common primary laser pulse 4, or secondary light pulses, which originated from different primary laser pulses 4. It can be seen that the temporal delay likewise fluctuates between a minimum value $t_{min}$ and a maximum value $t_{max}$. However, there is a certain time lag between the two upper curves and the lower curve resulting from the cycle of the light pulses in the optical assembly 1.

FIG. 3 shows a schematic representation of a second embodiment of an optical assembly 1 according to the invention. For reasons of clarity, only the pulsed light source 2 and its associated electronic components are here shown, but not the optical paths, in particular therefore, not the nevertheless existing pulse divider 5 and the delay element 8. They can be configured like in FIG. 1.

In the embodiment according to FIG. 3, a measuring device 19 is provided which delivers a signal 20 proportional to the pulse repetition rate of the oscillator or of the pulsed light source 2, respectively. This measuring device 19 can, for example, be formed as a frequency counter or as a phase detector. It therefore measures the present pulse repetition rate of the pulsed light source 2 represented by the center curve shown in FIG. 2

The measuring signal of the measuring device 19 is fed to a low pass filter 21. The low-pass filter blocks the high-frequency, selectively induced change of the pulse repetition rate of the pulsed light source 2. Instead, it only lets pass the low-frequency drift of the mean pulse repetition rate, which can occur, for example, due to thermal changes. The drift signal 22 is fed to a proportional-integral controller 23. This PID-controller 23 compares the drift signal 22 with a reference frequency signal 24 which is supplied by an external function generator 25. The reference frequency 24 is constant.

The output signal of the controller 23 is fed to a modulator 25 which in turn transmits a control signal 26 for controlling the pulse repetition rate to the pulsed light source 2 Overall, a control circuit 27 results, comprising the measuring device 19, the low pass filter 21, the controller 23 and the modulator 25. It is illustrated with dotted lines that a step motor driver 28 can be optionally provided, which likewise receives the signal from the controller 23 as an input signal, and in turn transmits a control signal 26' to the pulsed light source 2, for example, for adjusting a step motor determining the resonator length and thus the pulse repetition rate.

The mode of operation of the optical assembly 1 according to FIG. 3 is schematically shown in FIG. 4. It shows a diagram which is analogous to the time diagram shown in FIG. 2 and also represents the input voltage to the pulsed light source 2 in an upper curve. This input voltage again fluctuates periodically or sinusoidally, respectively, between a minimum value $V_{min}$ and a maximum value $V_{max}$.

It is shown in the center curve, how the pulse repetition rate changes when the temperature of the pulsed light source 2 increases or decreases, respectively. While the frequency of the induced changes in the pulse repetition rate and the amplitude of these induced changes remain constant, the mean value of the pulse repetition rate changes. The trend line of the mean value of the pulse repetition rate is in FIG. 4 denoted with 29. It initially rises, and with an increase in temperature then drops again.

A corresponding course is thereby also shown in the bottom curve, which represents the temporal delay between two secondary laser pulses 6, 7. Here as well, the mean value of the temporal delay initially rises, and subsequently decreases again. This change of the mean and thus also of the maximum or minimum delay is undesirable because it affects the precision of the temporal delay for subsequent applications.

A remedial measure for this problem is provided by the configuration of the optical assembly 1 illustrated in FIG. 3—as shown in FIG. 5. The control circuit 27 causes the input voltage, i.e. the control signal 26, 26' to not only periodically fluctuate between a minimum value $V_{min}$ and a maximum value $V_{max}$, but ensures that the mean value 30 of the control signal 26, 26' drifts according to the detected drift, in order to compensate for the temperature-related change of the pulse repetition rate. The result shows in the center curve in FIG. 5, according to which the pulse repetition rate fluctuates periodically as desired, however, without showing a rise or fall in drift (like in FIG. 4). Consequently, the temporal delay shown in the lower curve is accurate, i.e, without any drift upwards or downwards.

In the optical assembly 1, the resonator length of the pulsed light source 2 is changed by means of a piezo-electric actuator. For this piezo-electric actuator, the control voltage 26 may frequently not exceed or underrun a predefined voltage range. The circles in the first curve in FIG. 5 illustrate a situation in which the control voltage 26 would underrun this permitted range For this case, it is advantageous when the optical assembly 1 comprises a step motor being driven by the step motor driver 28 and permitting a comparatively coarse change in the resonator length of the pulsed light source 2. Subsequently, fine tuning of the resonator and thereby of the pulse repetition rate can again be performed by the piezo-electric actuator.

As a result, FIG. 5 in the center curve shows that the mean value of the pulse repetition rate is constant. The lower curve in FIG. 5 shows that the mean value of the temporal delay of the pulses is constant.

FIG. 6 shows a further embodiment for controlling the pulsed light source 2 in the optical assembly 1 according to the invention. It is here schematically shown that the pulsed light source 2 (like already in the previous embodiments) comprises a step motor 30 for a coarse adjustment of the resonator length (and thereby of the pulse repetition rate) and a piezo-electric actuator 31 for the fine adjustment of the resonator length, and thereby of the pulse repetition rate. The step motor 30 is controlled by the control signal 26' being supplied by the step motor driver 28.

The optical assembly 1 is provided with a frequency divider 32 adapted for electronically and/or optically determining the pulse repetition rate of the oscillator or the pulsed light source 2, respectively, and dividing it by a predetermined value. The signal of the frequency divider 32 is fed to a phase detector 33, which receives the signal from a frequency-modulated function generator 34 as another input signal. From these two input signals, the phase detector 33 generates a signal which is fed to a controller 23, which in turn can be configured as a PID-controller. Underneath the PID-controller 23 in FIG. 6, the output signal 24 of the function generator 34 is illustrated. The output signal of the controller 23 is supplied as a control signal 26 to both the piezo-electric actuator 31 of the pulsed light source 2 as well as to the step motor driver 28.

The embodiment according to FIG. 6 therefore differs from the previous embodiment in the frequency modulation of the reference frequency 24 provided by the function generator 34. The result of this configuration is shown in FIG. 7, which represents the course of four curves over time. The top curve represents the frequency modulated reference signal 24, i.e. the output of the function generator 33. By means of the control circuit 27 shown in FIG. 6, in particular the phase detector 34 and the downstream controller 23, the control signal 26 illustrated as the second curve in FIG. 7 is generated therefrom, which is fed to the piezo-electric actuator 31. This control signal increases linearly from a minimum frequency $V_{min}$ to a maximum frequency $V_{max}$. The resonator length of the pulsed light source 2 and thereby the pulse repetition rate therefore likewise increases linearly. It increases linearly from a minimum value $f_0$ to a maximum value $f_0+\Delta f$ when the piezo-electric actuator 31 decreases the resonator length. This is illustrated in the third curve in FIG. 7. The lowermost curve in FIG. 7 finally shows the effect of the changing pulse repetition rate to the delay time between the two different light pulses. It increases linearly from a minimum value $t_{min}$ to a maximum value $t_{max}$.

By varying the frequency of the reference signal 24, this configuration of the optical assembly 1 consequently permits the temporal delay not only in a manner fluctuating periodically, but with any characteristic, for example, linearly increasing or decreasing. It would be conceivable to have any arbitrary reference signal characteristic which, for example, would enable rough measurement in an irrelevant time range (fast reference frequency change) and precise measurement (slower reference frequency change) in a time range of relevance. By means of the rate of the frequency change of the reference signal 24, the increase of the control signal 26, the pulse repetition rate and the delay can be specifically influenced, since the pulse repetition rate of the pulsed light source 2 follows the modulated reference frequency 24. This configuration of the optical assembly 1 further allows for a very fast measuring method in which the pulse repetition rate is controlled by the piezo-electric actuator 31. The slow drift of the pulse repetition rate, however, can be corrected by the step motor 30.

FIG. 8 shows a further variant of the optical assembly 1 in a schematic representation. In this configuration, the pulse splitter 5 is already integrated into the pulsed light source 2. The pulsed light source 2 therefore comprises two different output ports 35, 36, via which the first or the second secondary light pulses 6, 7 exit the pulsed light source 2. Only the second secondary light pulses 7 are delayed relative to the first secondary light pulses by the delay element 8, which in turn can be a delay fiber line 9.

In the embodiment shown in FIG. 8, two optical amplifiers 37, 38 are also provided. The first amplifier 37 is passed through by the delayed second secondary light pulses 7, while the second amplifier 38 is passed through by the first secondary light pulses 6. In a first variant, the amplifiers 37, 38 are of the same design, so that they themselves do not lead to a further delay of the second secondary light pulses 7 relative to the first secondary light pulses 6. In another configuration, however, the amplifiers 37, 38 are designed differently so that they contribute to the delay of the light pulses.

Dashed arrows in FIG. 8 indicate, at which points of the optical assembly 1a dispersion compensation device 39 can optionally be arranged These dispersion compensation devices will be discussed later in more detail.

FIG. 9 shows a schematic representation of further configuration options of the optical assembly 1 according to the invention. The basic configuration of the optical assembly 1 above the dashed line in FIG. 9 corresponds to that of FIG. 8. Below the dashed line, however, other components are shown, which can optionally be integrated into the optical assembly 1. One electronic component that can be integrated into the optical assembly 1 is a trigger generator 40. It can be connected to the pulsed light source 2 and serves to capture data.

Further to the right, FIG. 9 shows different components that can be provided in addition to or in place of the amplifiers 37, 38 in the light paths of the first or second secondary light pulses 6, 7, respectively. These optionally existing optical or electronic components are a second-harmonic generator (SHG) 41, an amplitude modulator 42, a pulse picker 43, a non-linear medium 44, a pulse compressor 45 or an attenuator 46. Each of these components allows for an improved variation of the generated light pulses, for example, in view of their frequency, their pulse energy or their pulse duration, or an improvement in the precision of the delay between different light pulses obtained with the optical assembly 1.

FIGS. 10a to 10f represent different variants of the delay element 8 that can be used in the optical assembly 1 according to the invention. FIG. 10a shows a first configuration in which as a delay element 8, a delay fiber line 9 is used which simultaneously serves as a dispersion compensation device 39. For this purpose, two or more types of fibers 50a, 50b, 50c having different dispersion properties are coupled together so that the fiber line 9 has an overall dispersion of zero. In particular, so-called IDF fibers 50a (inverse dispersion-fibers), DCF fibers 50b (dispersion compensating fibers) and/or SMF fibers 50c (single-mode fibers), can be used both in a polarization-preserving, as well as in a non-polarization-preserving configuration.

FIG. 10b shows a second variant of a delay element 8. Here, the primary laser pulses 4 reach a pulse splitter 5 which is designed as a polarization beam splitter BS. A first portion in the form of first secondary light pulses 6 passes directly to an output 50d. A second portion in the form of second secondary light pulses 7 passes to a mirror M and from there back to the pulse splitter 5, before these second secondary light pulses 7 are also directed to the output 50d by the pulse splitter 5. The delay line presently represents the double passage through the line between the pulse splitter 5 and the mirror M. This line can comprise both dispersion compensation devices 39, as well as optical elements such as λ/4-wave plates 50e or Faraday rotators 50f in order to influence the polarization of the second secondary light pulses 7 such, that they are directed by the pulse splitter 5 to the output 50d as free of loss as possible.

As a delay fiber line 9 for the delay element 8, an optical fiber is used In a relatively simple configuration according to FIG. 10c, having effectively zero dispersion, e.g. a dispersion-shifted fiber, a photonic crystal fiber, a hollow core fiber or a fiber having reduced non-linearities.

FIG. 10d shows a variant of the delay element 8, in which a part 7 of the light from the pulse splitter 5 is cast onto a narrow-band mirror, in particular a fiber-Bragg grating BG, which reflects the light back to the pulse splitter 5. There, these light pulses 7, together with beam portion 6 freely passing the pulse splitter 5, are directed to the output 50d. Optical circulators can be used in the delay element 8, both in this embodiment as well as in the embodiment according to FIG. 10b.

FIG. 10e shows a further variant of a delay element 8 for the optical assembly 1 according to the invention. In this variant, an optical fiber leads to a reflection grating, a transmission grating or a prism combination K. In this, a group of prisms can simultaneously serve as a dispersion compensation device 39.

Finally, FIG. 10f shows a configuration of an optical assembly 1, in which only an amplifier 37 is provided in the path of the second secondary light pulses 7. This amplifier 37 causes a difference in path length for the second secondary light pulses 7 relative to the first secondary light pulses 6 and thus represents the delay element 8.

FIG. 11 shows a variant of the embodiment of the optical assembly 1, where the second secondary light pulses 7 after passing through the delay element 8 are again united with the first secondary light pulses 6 before the two groups of secondary light pulses 6, 7 are directed into a common optical amplifier 37. This common amplifier 37 is therefore configured to amplify both the first secondary light pulses 6 as well as the second secondary light pulses 7. Compared to the configuration in FIG. 8, this offers the advantage to be able to dispense with one of the two optical amplifiers 38, which makes the optical assembly 1 less complex and thereby more robust.

FIG. 12 in a schematic form shows an application of the optical assembly 1 illustrated in FIG. 11 After passing through the common optical amplifier 37, both the first as well as the second secondary light pulses 6, 7 reach a polarization beam splitter or a circulator 51, respectively the latter directs the secondary light pulses 6, 7 into an experimental setup 52, for example, a pump-probe experimental setup. Signal radiation 52, returning from the experiment setup 52 back to the circulator 51, is passed from there to a detector 54. From the change of the signal radiation 53 with the change in the temporal delay between the first and the second secondary light pulses 6, 7, information can be gathered regarding a sample examined. The experimental setup 52 can also comprise a terahertz transmitter and/or a terahertz receiver.

As an alternative to a circulator, a 50:50 beam splitter can be used or a combination of a polarization beam splitter (PBS) and a λ/4-wave plate. Polarization-maintaining circulators typically comprise a PBS and λ/4-wave plate or a Faraday rotator.

Finally, it is noted that the control circuits 27 of the above-described configurations can also be used independently of the measurement of a drift of the mean pulse repetition rate (e.g. also in the thermally insulated or stabilized embodiment of the optical assembly) in order to be able to thus adjust the pulse repetition rate in an ideal manner.

The invention claimed is:

1. Optical assembly (1) comprising a pulsed light source (2) for generating primary light pulses (4), a pulse splitter (5) for splitting said primary light pulses (4) into first and second secondary light pulses (6, 7), and a delay element (8) for delaying said second secondary light pulses (7) relative to said first secondary light pulses (6), where the pulse repetition rate of said pulsed light source (2) is variable, characterized in that said optical assembly (1) comprises
   a temperature insulation (12) for thermally insulating said delay element (8), and/or
   a temperature stabilizer (16) for thermally stabilizing said delay element (8), and/or
   a temperature compensator (13) for compensating a temperature-dependent change of an optical path length of said delay element (8) and/or
   a control circuit (27) for controlling said pulse repetition rate of said pulsed light source.

2. Optical assembly according to claim 1 characterized in that said temperature insulation (12) in addition to said delay element (8) also encloses said pulse splitter (5).

3. Optical assembly according to claim 1, characterized in that said temperature stabilizer (16) comprises a temperature sensor (14) as well as at least one heating element (17) and/or at least one cooling element (18).

4. Optical assembly according to claim 1, characterized in that said control circuit (27) comprises a frequency detector (19), a frequency counter (19) or a phase detector (19, 34).

5. Optical assembly according to claim 1, characterized in that said control circuit (27) comprises a function generator (25, 33) for pre-determining an external reference frequency (24).

6. Optical assembly (1), in particular according to claim 1, characterized in that an optical assembly (1) in the optical path of said first and/or said second secondary light pulses (6, 7) comprises one or more of the following elements: an amplifier (37, 38), an attenuator (46), a non-linear medium (44), a second-harmonic generator, SHG, (41), a pulse compressor (45), a pulse picker (43), an amplitude modulator (42), or a dispersion compensator (39).

7. Optical assembly according to claim 6, characterized in that said common amplifier (37) is provided for said first and said second secondary light pulses (6, 7).

8. Method for generating light pulses (6, 7) with a variable delay between different light pulses (6, 7), comprising the following steps:
generating primary light pulses (4) with a pulsed light source (2),
splitting said primary light pulses (4) into first and second secondary light pulses (6, 7) by a pulse splitter (5),
delaying said second secondary light pulses (7) relative to said first secondary light pulses (6) by a delay element (8), and
changing a pulse repetition rate of said pulsed light source (2),
characterized in that
the temperature of said delay element (8) is maintained constant by a temperature stabilizer (16) and/or
a temperature-dependent change of an optical path length of said delay element (8) is compensated by a temperature compensator (13) and/or
a drift of a mean pulse repetition rate of said pulsed light source (2) is determined and controlled.

9. Method according to claim 8, characterized in that said pulse repetition rate of said pulsed light source (2) is determined by a frequency detector (19), a frequency counter (19) or of a phase detector (19, 34).

* * * * *